United States Patent [19]

Lattin et al.

[11] Patent Number: 5,366,983

[45] Date of Patent: Nov. 22, 1994

[54] USE OF QUATERNARY AMMONIUM COMPOUNDS TO REMOVE SALMONELLA CONTAMINATION FROM MEAT PRODUCTS

[75] Inventors: Danny L. Lattin; Philip J. Breen; Cesar M. Compadre, all of Little Rock; E. Kim Fifer, North Little Rock; Michael F. Slavik, Springdale; Hamid Salari, Little Rock; Phillip V. Engler, Fayetteville, all of Ark.

[73] Assignee: The Board of Trustees of The University of Arkansas, Little Rock, Ark.

[21] Appl. No.: 863,445

[22] Filed: Apr. 3, 1992

[51] Int. Cl.$^5$ .............................................. A01N 43/40
[52] U.S. Cl. ..................................................... 514/358
[58] Field of Search ........................................ 514/358

[56] References Cited

U.S. PATENT DOCUMENTS 4,165,375  8/1979  Berger et al. ................. 514/358

FOREIGN PATENT DOCUMENTS 479925  3/1938  United Kingdom ................ 514/358

OTHER PUBLICATIONS

The Merck Index, 10th Ed. (1983) #1987.
Nakagawa et al., C.A. vol. 92 (1980) 92:162,167m.
Varga, C.A., vol. 78 (1973) 106,462c.
Hofmann et al., C.A. vol. 73 (1970) 119,686a.

*Primary Examiner*—Allen J. Robinson
*Attorney, Agent, or Firm*—Hermann Ivester

[57] ABSTRACT

A composition and method for removing and preventing Salmonella contamination of meat products, in particular poultry. The composition comprises an effective amount of a quaternary ammonium compound in an aqueous solution. The quaternary ammonium compound are selected from the group consisting of alkylpyridinium, tetra-alkylammonium, and alkylalicyclic ammonium salts. Preferably, the quaternary ammonium compounds are cetylpyridinium chloride (CPC) and cetylpyridinium bromide (CPB). The method comprises treating meat and poultry products with an effective amount of the quaternary ammonium compound in an aqueous solution. Mutagenicity studies are also disclosed.

18 Claims, 4 Drawing Sheets

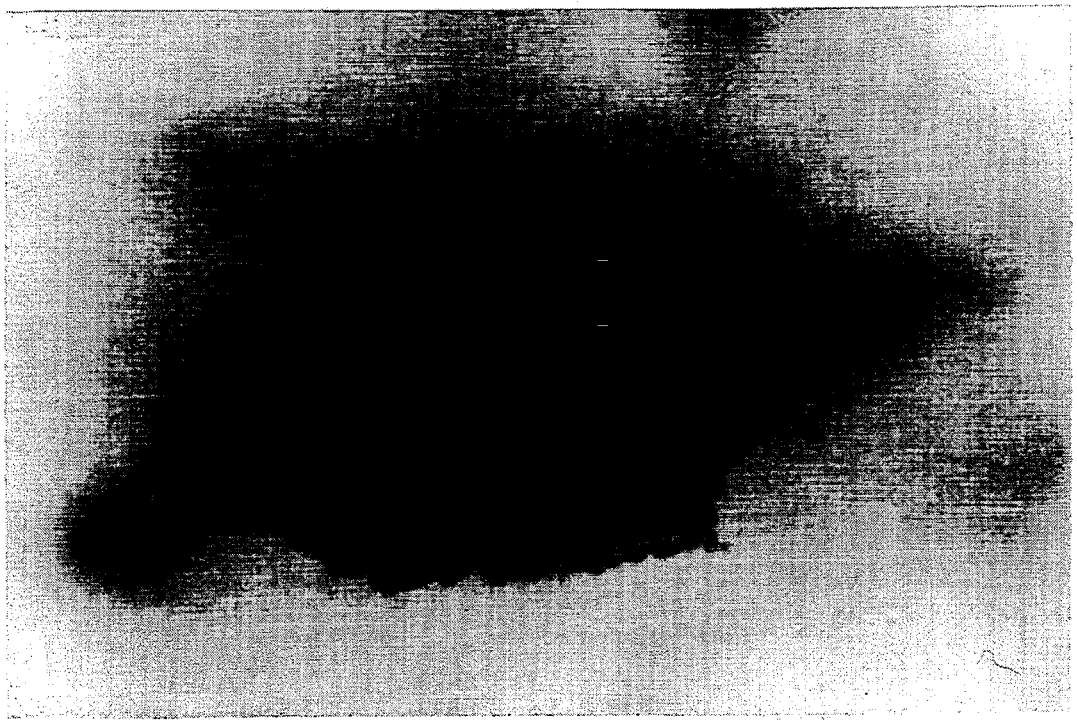
FIG.IA
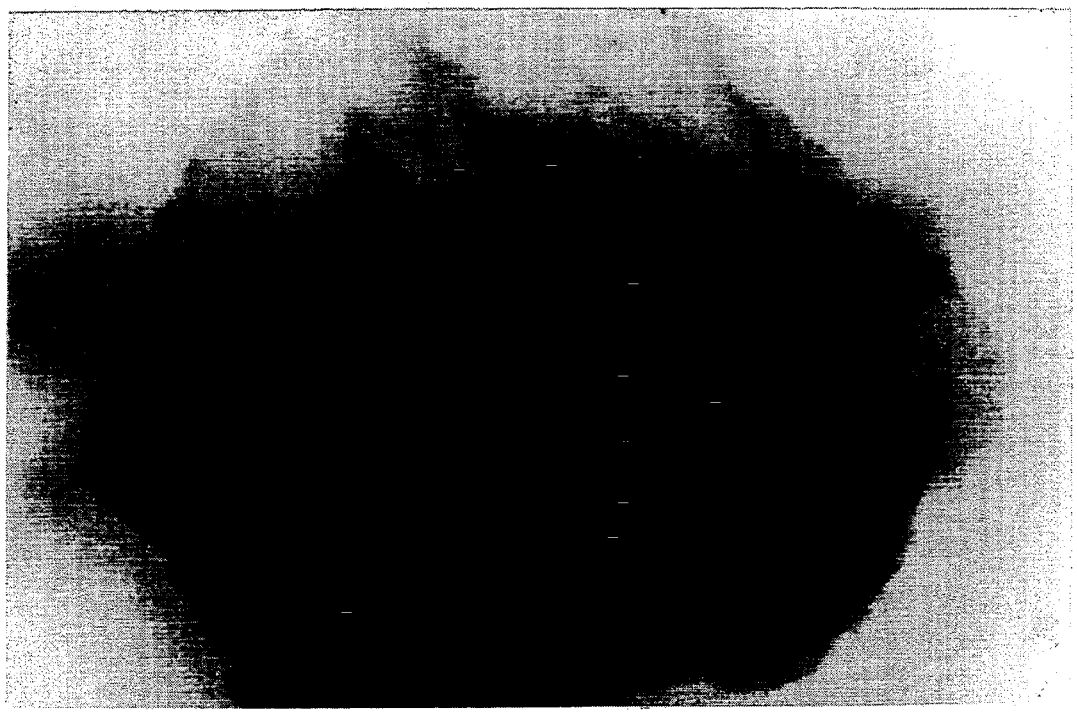
FIG.IB

USE OF QUATERNARY AMMONIUM COMPOUNDS TO REMOVE SALMONELLA CONTAMINATION FROM MEAT PRODUCTS

BACKGROUND OF THE INVENTION

The present invention relates to a method and composition for removing Salmonella contamination from food products. More specifically, the present invention relates to a method which utilizes quaternary ammonium compounds for preventing and removing Salmonella contamination from meat and poultry products.

Prevention of food-borne illness via microbiological contamination during processing is of major concern to the poultry and meat processing industry, regulatory agencies, and the consuming public. Salmonella contamination is of special concern in the poultry and meat processing industry. Nontyphoidal salmonellosis is a continuing public health problem in the United States and throughout the world. Reports estimate that 2 to 4 million cases of salmonellosis occur annually in the United States, and associated annual patient-care costs may exceed $2 billion.

In their efforts to provide a product completely free of microbiological contamination, poultry and meat processors have encountered major difficulty in removing those microorganisms that adhere or attach rigorously to poultry and meat tissues intended as food products. Like many other microorganisms, Salmonella are capable of becoming very firmly attached to many surfaces that are used for food such as poultry and meat tissues. The microorganisms that do not attach can be rinsed off easily.

On the other hand, those microorganisms that become strongly attached cannot be removed by mere rinsing and become more resistant to removal by chemical or physical means. This phenomenon of strong attachment or adherence has been well documented and studied, but the chemical and biochemical mechanisms involved in bacterial attachment remain unclear. Firstenberg-Eden et al., "Attachment of Certain Bacterial Strains to Chicken and Beef Meat.", J. Food Safety 1:217-228 (1978); Schwach et al., "Use of Scanning Electron Microscopy to Demonstrate Microbial Attachment to Beef and Beef Contact Surfaces", J. Food Sci. 47: 1401-1405 (1982); Soerjadi et al., "Adherence of Salmonellae and Native Gut Microflora to the Gastrointestinal Mucosa of Chicks", Avian Dis. 26:576-584 (1982); Lillard, "Bacterial Cell Characteristics and Conditions Influencing Their Adhesion to Poultry Skin", J. Food Protect. 48:803-807 (1985); Lillard, "Role of Fimbriae and Flagella in the Attachment of *Salmonella typhimurium* to Poultry Skin", J. Food Sci. 51:54-56 (1986); Kristiansen et al., "Toxins, Putative Cell Adhesions and Fibronectin Binding Properties of *Salmonella Dublin*", Acta Path. Microbiol. Immunol. Scand., Sect. B 95:57-63 (1987); and Finlay et al., "Epithelial Cell Surfaces Induce Salmonella Proteins Required for Bacterial Adherence and Invasion" Sci. 243:940-943 (1989).

A variety of approaches have been utilized to eliminate Salmonella contamination, including vaccination of poultry, administration of antibiotics, and modifications in the processing of poultry to minimize cross-contamination among carcasses. Use of various acids in the scald tank, heat treatment by high temperature scalds, as well as the addition of chlorine to the scald tank have also been used in an attempt to solve the problem of Salmonella contamination of meat products. However, some of the existing processes may adversely effect the appearance, color, flavor, and/or texture of meat products. More importantly, existing technologies are not completely effective in removing all of the attached microorganisms from poultry and meat tissues. See, National Research Council, Meat and Poultry Inspection: The Scientific Basis of the Nation's Program, Report of the Food and Nutrition Board's Committee on the Scientific Basis of the Nation's Meat and Poultry Inspection Program, National Academy Press, Washington, D.C., 209 pp., (1985); and National Research Council, Poultry Inspection: The Basis for a Risk-Assessment Approach, Report of the Food and Nutrition Board's Committee on Public Health Risk Assessment of Poultry Inspection Programs, National Academy Press, Washington, D.C., 167 pp., (1987).

Accordingly, a more effective process for the removal and prevention of Salmonella contamination of meat products as well as the characterization of the mechanisms involved in microbial surface attachment would be of tremendous value to the food processing industry.

SUMMARY OF THE INVENTION

The present invention provides a composition and method for the removal and prevention of Salmonella contamination of meat products, in particular poultry. The composition comprises an effective amount of a quaternary ammonium compound in an aqueous solution. The quaternary ammonium compound is selected from the group consisting of alkylpyridinium, tetraalkylammonium, and alkylalicyclic ammonium salts. The method of the present invention involves treating meat and poultry products with an effective amount of the quaternary ammonium compound in an aqueous solution. Preferably, the method is conducted at temperatures ranging from approximately 4° C. to about 100° C.

The quaternary ammonium compounds of the present invention, all of which are cationic surfactants, are effective in both inhibiting attachment of Salmonella to, and removing the attached Salmonella from poultry tissues. The quaternary ammonium cationic surfactants, particularly cetylpyridinium chloride (CPC) and cetylpyridinium bromide (CPB) are especially effective in detaching strongly bound Salmonella. Further, the concentrations of these compounds that are effective in removing the Salmonella from tissues nave proven to be equally effective in inhibiting the attachment of the microorganism.

The present invention has potential widespread application in the food processing industry and for home use. The quaternary ammonium compounds are readily available, and the cost of carrying out the method of the present invention is low relative to existing processes;. No stringent conditions of high temperature or low pH are required with the use of these compounds.

Unlike existing treatments, the use of quaternary ammonium compounds; does not alter the appearance, color, taste, or texture of the meat product. Low concentrations of the quaternary ammonium compounds are effective in reversing and/or preventing Salmonella contamination. With respect to the safety of the quaternary ammonium compounds, studies show no evidence of mutagenicity with CPC, even after heating at high temperatures. Further, CPC is already approved for human use in products for oral ingestion such as Cepacol® Lozenges.

In one embodiment of the present invention, the meat products include poultry.

In another embodiment, the quaternary ammonium compounds are cationic surfactants.

In another embodiment, the quaternary ammonium compounds are at a concentration ranging from approximately $1\times10^{-6}$ M to $4\times10^{-4}$ M.

In another embodiment of the present invention, the meat product is treated with an effective amount of the quaternary ammonium compound in an aqueous solution for approximately 10 minutes to about 60 minutes.

Additional features and advantages of the present invention are further described, and will be apparent from the detailed description from the presently preferred embodiments.

BRIEF DESCRIPTION OF THE DRAWINGS

FIG. 1A is a photomicrograph of typical buccal epithelial cells incubated with *Salmonella typhimurium* and treated with buffer only. The small dark spots on the cells represent *S. typhimurium*.

FIG. 1B is a photomicrograph of typical buccal epithelial cells incubated with *S. typhimurium* and treated with a quaternary ammonium compound, cetylpyridinium chloride, and a buffer. The small dark spots on the cells represent *S. typhimurium.*

DETAILED DESCRIPTION OF THE PRESENTLY PREFERRED EMBODIMENTS

The present invention provides a composition and method for removing and preventing Salmonella contamination of meat and poultry products. The composition comprises an effective amount of a quaternary ammonium compound in an aqueous solution. The quaternary ammonium compound is selected from the group consisting of alkylpyridinium, tetra-alkylammonium, and alkylalicyclic ammonium salts.

Alkylpyridinium is represented by the structural formula (I):

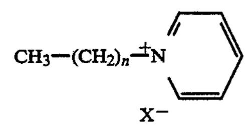

(I)

wherein n is 9–21; and $X^-$ is a halide.

Tetra-alkylammonium is represented by the structural formula (II):

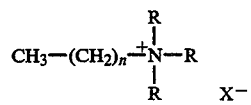

(II)

wherein n is 9–21; R is selected from the group consisting of $CH_3$ and $C_2H_5$; and $X^-$ is a halide.

Alkylalicyclic ammonium salts are represented by the structural formula (III):

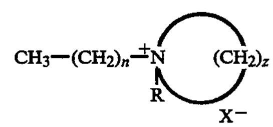

(III)

wherein n is 9–21; Z is 4–5; R is selected from the group consisting of $CH_3$ and $C_2H_5$; and $X^-$ is a halide.

A variety of quaternary ammonium compounds, all of which are cationic surface-active agents (or surfactants), were evaluated for their effectiveness in removing attached Salmonella from poultry tissues as well as preventing the attachment of Salmonella to tissues. Both in vitro (non-poultry) and poultry models are studied. Of the quaternary ammonium compounds studied, cetylpyridinium chloride (CPC) and cetylpyridinium bromide (CPB) were the most effective in detaching the strongly bound Salmonella from the tissue. In this regard, CPC was effective at concentrations that are lower than its bactericidal concentration against Salmonella. At slightly higher levels, CPC was extremely effective in reversing Salmonella contamination of tissue by killing the microorganisms, even the usually impenetrable surface-adherent microcolonies. Equally as important, CPC exhibited no evidence of mutagenicity, even when heated at high temperatures.

For purposes of the following discussion, the removal and prevention of Salmonella contamination from poultry models is emphasized. However, it is intended that other meat products may be used in practicing the present invention.

By way of example, and not limitation, the following examples serve to further illustrate the present invention in its preferred embodiments.

EXAMPLE

Detachment of Salmonella from Human Buccal Epithelial Cells

Studies were conducted on the attachment of *Salmonella typhimurium* to human buccal epithelial cells using the modified procedure of Boussard et al., International J. Pharmaceutics 53: 253–256 (1989). In this study, the activities of cationic and anionic surfactant compounds as well as certain chelating agents were compared on the detachment of *S. typhimurium* from epithelial cells.

Figure 2:
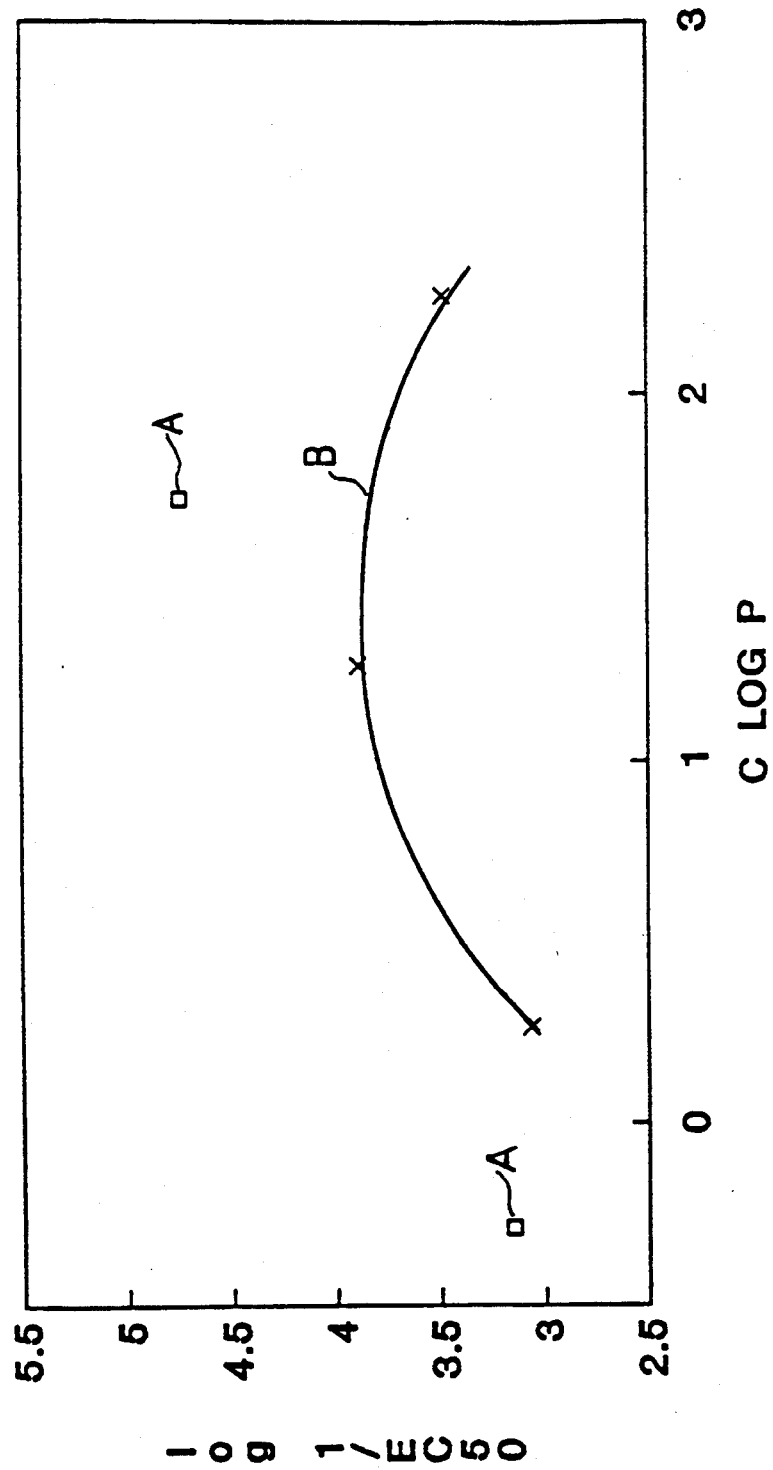
FIG. 2 is a graph illustrating the effect of hydrophobicity on the detachment of *S. typhimurium*. Plot A represents pyridinium quaternary ammonium compounds (CPC and dodecylpyridinium chloride (DPC)). Plot B represents trimethyl quaternary ammonium compounds dodecyltrimethylammonium bromide (DTMAB), tetradecyltrimethylammonium bromide (TTMAB), and hexadecyltrimethylammonium bromide (HTMAB).

To this end, bacteria were grown on nutrient agar for 16 hours at 37° C. The cells were suspended in 0.008 M phosphate buffered saline (PBS) at pH 7.2 and washed two times at 4500 rpm for 10 minutes. The last suspension was diluted in PBS to obtain a cell concentration of 0.5 to $1 \times 10^9$ cells/ml. Human epithelial cells were obtained by swabbing the buccal surface of a healthy, nonsmoking donor. The epithelial cells were suspended in PBS and washed two times at 4500 rpm for 10 minutes. The number of living cells was estimated and the suspension diluted to 0.5 to $1 \times 10^5$ cells/ml.

Next, the suspension of the human buccal cells was mixed with an equal volume of the bacterial suspension (3.0 ml), or PBS (0.8 ml). Contact was allowed for 1.5 hours at 35° C. under agitation. The mixtures were then centrifuged for 10 minutes at 4500 rpm. Each suspension, 1.0 ml, was transferred into Eppendorf vials and washed with PBS at 1500 rpm for 10 minutes. After the washing, the cells were treated with 1.0 ml PBS or 1.0 ml of the test chemical solution. Treatment was performed by suspending and vortexing on a low speed for 30 seconds followed by centrifugation at 1500 rpm for 10 minutes.

After the treatment, the cells were washed once with PBS and then 20 μl of erythrosin B was added to each vial. The suspension was centrifuged at 1500 rpm for 10 minutes, and the cells were washed twice under the same conditions. The final pellet was suspended in 300 μl of PBS. This suspension was spread out onto microscope slides and dried overnight at room temperature. After counter staining with methylene blue, the slides were microscopically examined under oil immersion.

The effects of various chemicals on attachment of S. typhimurium to human buccal epithelial cells are shown in Table A-1. The chemicals studied were hexadecyltrimethylammonium bromide (HTMAB), tetradecyltrimethylammonium bromide (TTMAB), dodecyltrimethylammonium bromide (DTMAB), cetylpyridinium bromide (CPB), dc, decylpyridinium chloride (DPC), and sodium dodecylsulfate (SDS). The results of Table A-1 demonstrate a concentration-dependent action of SDS and the quaternary ammonium compounds (all the remaining compounds). At 50 μg/ml, all compounds tested produced a decrease in bacterial attachment to the epithelial cells. CPB, however, was the only agent that produced a significant decrease in bacterial attachment at a concentration of 10 μg/ml.

TABLE A-1

Effect of various chemicals on attachment of Salmonella typhimurium ATCC 14028 to Human buccal epithelial cells. The adherence is expressed as mean (Mean ± SD) value of attached bacteria by counting 30 to 50 epithelial cells.

| Treatment | Concentration (ug/ml) | | | | | | | | |
|---|---|---|---|---|---|---|---|---|---|
| | 0 | 5 | 10 | 25 | 50 | 75 | 100 | 250 | 500 |
| HTMAB | | | | | | | | | |
| a) | 61 ± 24 | — | — | — | 48 ± 20 | — | 33 ± 24 | — | — |
| b) | 52 ± 31 | 49 ± 21 | — | — | — | — | 32 ± 19 | — | cytotoxic |
| TTMAB | | | | | | | | | |
| a) | 52 ± 30 | — | 39 ± 26 | — | 28 ± 14 | — | 12 ± 8 | — | — |
| b) | 50 ± 20 | 37 ± 20 | — | 24 ± 13 | — | — | 18 ± 8 | — | — |
| DTMAB | | | | | | | | | |
| a) | 68 ± 33 | — | 76 ± 43 | — | 19 ± 18 | — | 23 ± 18 | — | — |
| b) | 52 ± 21 | — | — | 41 ± 19 | 26 ± 18 | 30 ± 18 | — | — | — |
| CPB | 72 ± 46 | — | 28 ± 28 | 23 ± 17 | 25 ± 10 | — | — | — | — |
| DPC | | | | | | | | | |
| a) | 61 ± 32 | — | 70 ± 35 | — | 46 ± 28 | — | 34 ± 18 | — | — |
| b) | 47 ± 26 | — | — | 55 ± 23 | — | 34 ± 20 | — | — | 14 ± 10 |
| SDS | | | | | | | | | |
| a) | 49 ± 21 | — | — | 43 ± 25 | 26 ± 19 | — | 28 ± 16 | — | — |
| b) | 41 ± 12 | — | — | — | — | — | 22 ± 16 | — | cytotoxic |

The results of treatment with various chelating agents are shown in Table A-2.

TABLE A-2

Effect of Na$_2$-EDTA, and EGTA on attachment of Salmonella typhimurium ATCC 14028 to Human buccal epithelial cells. The adherence is expressed as mean (Mean ± SD) value of attached bacteria by counting 30 to 50 epithelial cells.

| Treatment | Concentration (ug/ml) | | | | | |
|---|---|---|---|---|---|---|
| | 0 | 500 | 1250 | 2500 | 5000 | 10,000 |
| Na$_2$-EDTA | | | | | | |
| a) | 49 ± 23 | — | — | 35 ± 18 | 26 ± 16 | 31 ± 14 |
| b) | 45 ± 21 | 43 ± 21 | 22 ± 12 | — | 27 ± 14 | — |
| EGTA | | | | | | |
| a) | 20 ± 7 | — | — | 22 ± 1 | 20 ± 10 | 20 ± 8 |
| b) | 31 ± 13 | — | — | 31 ± 16 | 30 ± 11 | 27 ± 11 |

Results indicate that treatment with disodium ethylenectiaminetetraacetate (Na$_2$-EDTA) was highly effective at a concentration of 1250 μg/ml and a further increase in Na$_2$-EDTA concentration did not improve this effect. However, ethylenebis(oxyethylenenitrilotetraacetic acid (EGTA) treatment had no significant effect on reducing the bacterial attached to the epithelial cells.

Additional studies on the detachment of Salmonella typhimurium from human buccal epithelial cells were conducted. In this study, CPC, DPC, and HTMAB, TTMAB DTMAB, were evaluated.

S. typhimurium ATCC 14028 was grown in nutrient broth (BBL Microbiology system, Cockeysville, Md.) for 16 hours at 37° C. The cells were centrifuged and washed twice with 0.008 M phosphate buffered saline (PBS, at pH 7.2) at 4500 rpm for 10 minutes. The last suspension was diluted in PBS to obtain a cell concentration 0.5 to $1\times10^9$ cells/ml using spectrophotometric measurement. Human epithelial cells were obtained by swabbing the buccal surface of a healthy, nonsmoking donor. The epithelial cells were suspended in PBS and washed two times at 4500 rpm for 10 minutes. The number of living cells was estimated and the suspension was diluted to 0.5 to $1\times10^5$ cells/ml.

The suspension of the human buccal cells was mixed with an equal volume of the bacterial suspension (3.0 ml), or PBS (0.8 ml) in 10 ml Erlenmeyer flasks. Contact was allowed for 1.5 hours at 35° C. under agitation. After incubation, 1.0 ml of each suspension was transferred into an Eppendorff vial, centrifuged at 3000 rpm for 10 minutes, and washed with PBS. The cells were treated with 1.0 ml PBS or 1.0 ml of the test chemical solution. Treatment was performed by suspending, gently vortexing, and centrifuging at 1500 rpm for 10 minutes. After the treatment, the cells were washed and placed on microscopic slides for examination.

A photomicrograph of a buccal epithelial cell prepared according to the method described above but not treated with a cationic surfactant is illustrated in FIG. 1A. A similar buccal epithelial cell treated with 10 mcg/mL of CPC solution, and shown in FIG. 1B, shows a reduction in the number of Salmonella on the cell.

The overall results of this study are shown in Table A-3. CPC was found to be the most active compound, followed in decreasing order by TTMAB, HTMAB, DPC, and DTMAB. CPC was active at concentrations as low as 5 μg/ml. TTMAB exhibited activity at a concentration of 25 μg/ml. The remaining compounds were active at concentrations of 100 μg/ml or higher. These results were consistent with previously described experiments. Although not shown in Table A-3, a mixture of CPC and $Na_2$-EDTA showed no significant improvement over the effects of each compound, individually.

Results from Tables A-1 and A-3 indicated that a concentration of 10 mcg/mL of each of CPC and CPB effectively removed an average of 65% of Salmonella from human buccal epithelial cells.

TABLE A-3

Effect of various chemicals on attachment of Salmonella typhimurium ATCC 14028 to human buccal epithelial cells. The adherence is expressed as mean (Mean ± SD) value of attached bacteria by counting 30 to 50 epithelial cells.

| Treatment | Concentration (ug/ml) | | | | | | | |
|---|---|---|---|---|---|---|---|---|
| | 0 | 2.5 | 5 | 10 | 25 | 50 | 75 | 100 |
| CPC | 80 ± 48 | 73 ± 55 | 42 ± 22 | 28 ± 10 | — | — | — | — |
| HTMAB | 145 ± 46 | — | — | — | — | — | — | 82 ± 35 |
| TTMAB | | | | | | | | |
| a) | 93 ± 29 | — | — | — | — | — | 72 ± 53 | 42 ± 22 |
| b) | 124 ± 66 | — | — | — | 91 ± 66 | 53 ± 34 | — | 26 ± 14 |
| DTMAB | | | | | | | | |
| a) | 135 ± 60 | — | — | — | — | — | — | 92 ± 58 |
| b) | 102 ± 56 | — | — | — | — | 113 ± 85 | — | 74 ± 56 |
| c) | 116 ± 74 | — | — | — | — | — | 102 ± 59 | — |
| DPC | | | | | | | | |
| a) | 182 ± 83 | — | — | — | — | — | — | 129 ± 87 |
| b) | 209 ± 68 | — | — | — | — | — | — | — |

| Treatment | Concentration (ug/ml) | | | | | | |
|---|---|---|---|---|---|---|---|
| | 150 | 175 | 200 | 250 | 300 | 325 | 450 |
| CPC | — | — | — | — | — | — | — |
| HTMAB | — | 57 ± 33 | — | 33 ± 19 | — | — | — |
| TTMAB | | | | | | | |
| a) | — | 28 ± 10 | — | — | — | — | — |
| b) | — | — | — | — | — | — | — |
| DTMAB | | | | | | | |
| a) | — | — | — | 63 ± 35 | — | 68 ± 39 | — |
| b) | — | — | 60 ± 43 | — | — | — | — |
| c) | 80 ± 59 | — | — | — | 54 ± 35 | — | — |
| DPC | | | | | | | |
| a) | — | 110 ± 73 | — | 62 ± 50 | — | — | — |
| b) | 141 ± 66 | — | — | — | 61 ± 34 | — | 54 ± 23 |

$EC_{50}$ results for a group of quaternary ammonium compounds that are cationic surfactants are shown below in Table A-4. $EC_{50}$ represents the inverse measurement of the potency of a compound. $EC_{50}$ values were determined by a nonlinear regression of the detachment effect versus the cationic surfactant concentration data from Table A-3. $EC_{50}$ results showed that CPC had the highest potency (or lowest $EC_{50}$) for the detachment effect. T tests on the $EC_{50}$ results for the cationic surfactants indicated that all of them differed at the $p\leq0.01$ level, thus indicating highly significant differences.

TABLE A-4

DETACHMENT SUMMARY
(PCNONLIN Sigmoidal Emax, ratio algorithm, actual SD's)

| Compound | $EC_{50}$ (±SD) $\underline{M} \times 10^5$ | S (±SD) | #pts | r |
|---|---|---|---|---|
| CPC | 1.81 ± 0.36 | 2.21 ± 0.80 | 3 | .958 |
| HTMAB | 33.3 ± 1.4 | 1.40 ± 0.20 | 3 | .989 |
| TTMAB | 12.9 ± 0.39 | 1.81 ± 0.12 | 3 | .998 |
| DTMAB | 86.8 ± 11.2 | 1.14 ± .20 | 8 | .937 |
| DPC | 71.6 ± 6.3 | 1.56 ± .31 | 6 | .955 |

FIG. 2 illustrates the effect of hydrophobicity on the detachment of S. typhimurium. As shown, log $1/EC_{50}$ (a measure of the effectiveness of detaching Salmonella from buccal epithelial cells) is plotted against C Log P, which represents a constant times the log of the oil/water partition coefficient of each compound (a measure of lipophilicity and hydrophobicity). Results suggest two families of curves for detachment. The pyridinium quaternary ammonium compounds (CPC and DPC) lie in the higher curve (designated "A"), while the trimethyl quaternary ammonium compounds (DTMAB, TTMAB, and HTMAB) fall on a parabolic curve (designated "B") with maximum effectiveness at intermediate hydrophobicity.

EXAMPLE 2

Prevention of the Attachment of Salmonella to Human Buccal Epithelial Cells

In order to determine whether the most effective quaternary ammonium compound, CPC, had the ability to prevent, as well as reverse, contamination of buccal epithelial cells with Salmonella, the following experiment was performed.

The Salmonella suspension and the human buccal epithelial cells were prepared according to the method described in the detachment experiments of Example 1, except that only the control buccal epithelial cells were suspended in PBS and washed twice at 4500 rpm for 10 minutes. The remaining buccal epithelial cells in the experiment were suspended in various concentrations of CPC in PBS before washing and centrifugation. The exposure of the buccal epithelial cells to the Salmonella suspension and all subsequent procedures were performed according to the method described in Example 1. The results are shown below in Table B-1.

TABLE B-1

| Prevention of the Attachment of Salmonella to Buccal Epithelial Cells | |
|---|---|
| Conc. of CPC (mcg/mL) | Counts/con |
| 100 | 30/70 |
| 100 | 23/74 |
| 10 | 26/70 |
| 10 | 24/74 |
| 5 | 41/71 |
| 2.5 | 62/71 |

In Table B-1, the column "counts/con" refers to the number of bacteria present on a buccal epithelial cell compared to the number of bacteria present on a cell not treated with CPC, but otherwise subjected to the same conditions and run on the same day as the experimental buccal epithelial cells. Table B-1 shows that exposure of buccal epithelial cells to CPC concentrations of 10 mcg/mL and higher prevented around 65% of the contamination found in the untreated cells. Using a t test analysis, this result was significant at the p=0.005 level. Further, this result, an average of 65% reversal of Salmonella contamination on buccal epithelial cells with 10 mcg/mL CPC, is identical to the detachment results shown in Example 1. CPC is thus equally effective in removing Salmonella from tissue and inhibiting their attachment.

EXAMPLE 3

Minimum Inhibitory Concentrations

Minimum growth inhibitory concentrations (MICs) of quaternary ammonium compounds and $Na_2$-EDTA for Salmonella were determined using Mueler Hinton broth (BBL Microbiology system, Cockeysville, Md.) and by the macrodilution method established by the National Committee for Clinical Laboratory Standards (NCCLS). Escherichia coli ATCC 25922 and Staphylococcus aureus ATCC 29213 were included in each assay as reference strains. The acceptable MIC of ampicillin for E. coli and S. aureus by NCCLS are 2–8 μg/ml and 0.5–2 μg/ml, respectively. The ranges of the MICs for a variety of quaternary ammonium compounds and EDTA for S. typhimurium are shown below in Table C-1.

TABLE C-1

Susceptibility of Salmonella typhimurium ATCC 14028 to Quaternary Ammonium Compounds and EDTA

| MIC (μg/ml) | | | | | |
|---|---|---|---|---|---|
| CPC | TTMAB | HTMAB | DTMAB | DPC | $Na_2$-EDTA |
| 64 | 64 | 64 | 156 | — | — |
| 40 | 60 | 60 | 150 | — | — |
| 50 | — | — | — | — | 625 |
| 50 | — | — | — | 80 | — |

EXAMPLE 4

Effect On Viability of Salmonella In Suspension

Studies were conducted on the antimicrobial activity against Salmonella typhimurium on human buccal epithelium cells by HTMAB, TTMAB, DTMAB, DPC, CPC, and chelating agents, $Na_2$-EDTA and EGTA.

Salmonella typhimurium ATCC 14028 was used for these studies and prepared as follows. A 16 hour culture in nutrient broth (BBL) was centrifuged at 15,000 rpm for 10 minutes at 4° C. The deposit was washed once with 0.04 M potassium phosphate buffer (PPB) at pH 7.0 and resuspended in fresh PPB to contain $1-2\times10^9$ bacteria/ml. Samples (1.0 ml) of this suspension were added into a 1.8 ml Eppendorff vial and centrifuged at 14,000 rpm for 4 minutes. The pellets were first suspended in 1.0 ml of PPB or 1.0 ml of an appropriate concentration of test chemical solution, and then centrifuged and washed with the buffer under the same conditions. After washing, the samples of bacterial suspensions were appropriately diluted in PPB. Duplicate 0.05 ml samples were withdrawn and immediately added onto nutrient agar plates. Colonies were counted after 24 hours incubation at 37° C. Results are reported in Table D-1 below as colony forming units per milliliter (CFU/ml).

Figure 3:
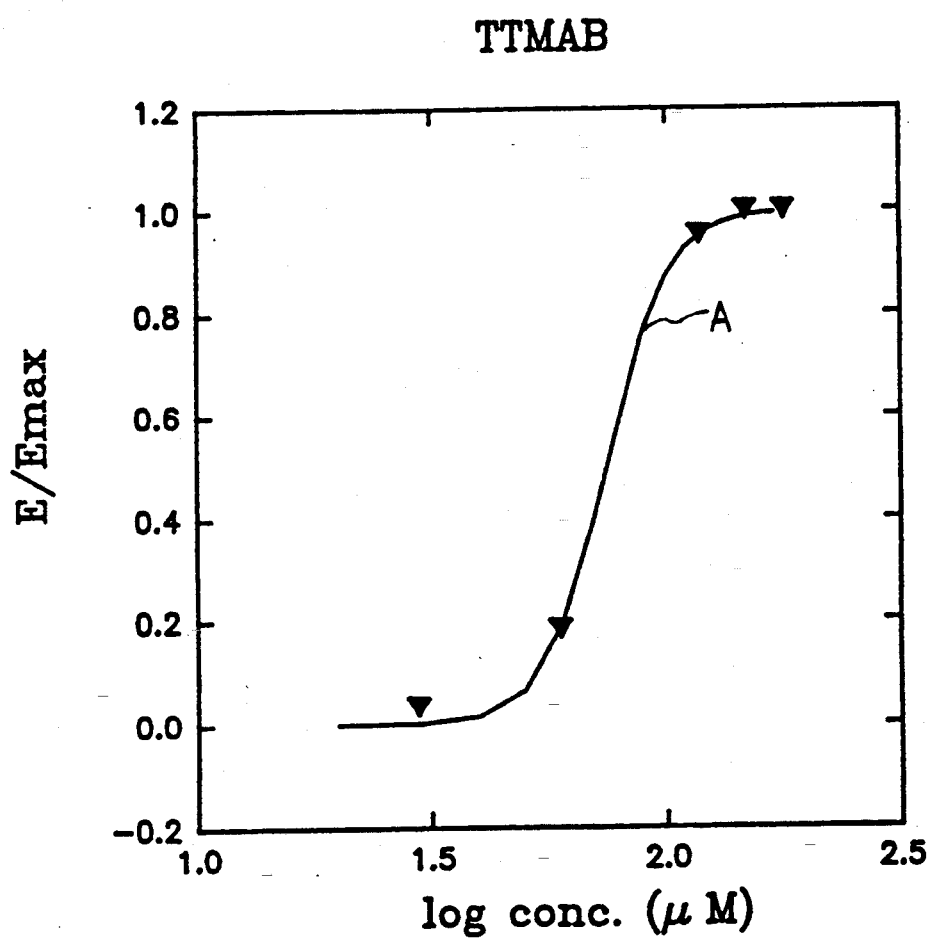
FIG. 3 is a graph representing E/Emax (effect/maximum possible effect) versus log cationic surfactant concentration of TTMAB (μM). Plot A represents 5 data points derived from TTMAB concentration values in Table D1.

Table D-1 shows the bactericidal activities of a variety of quaternary ammonium compounds on S. typhimurium. $EC_{50}$ values for four of the compounds were calculated from the bactericidal activity of the compounds as a function of molar concentration by a nonlinear regression algorithm. These results are shown in Table D-2. The $EC_{50}$ for DPC could not be calculated since there were only two data points. However, the raw data in Table D-1 suggests that DPC's bactericidal effect against Salmonella is not great. FIG. 3 illustrates the good fit of a typical data set representing TTMAB to a theoretical sigmoidal Emax model.

TABLE D-1

Antimicrobial activities of Quaternary ammonium compounds (QAC) on *Salmonella typhimunim* ATCC 14028. The bacterial viability is expressed as colony forming units per milliliter (CFU/ml). Values are the means of three determinations (mean ± SD).

| Compound | Concentration (ug/ml) | | | | | |
|---|---|---|---|---|---|---|
| | 0 | 10 | 20 | 30 | 40 | 50 |
| HTMAB | | | | | | |
| a) | $1.10 \pm 0.09 \times 10^9$ | $1.06 \pm 0.08 \times 10^9$ | — | — | — | — |
| b) | $1.12 \pm 0.17 \times 10^9$ | — | $3.23 \pm 0.38 \times 10^8$ | — | $3.6 \pm 2.8 \times 10^6$ | — |
| c) | $2.07 \pm 0.15 \times 10^9$ | — | — | — | $667 \pm 140$ | $50 \pm 50$ |
| d) | $1.64 \pm 0.14 \times 10^9$ | $1.67 \pm 0.12 \times 10^9$ | $6.35 \pm 1.03 \times 10^8$ | — | $4.6 \pm 1.9 \times 10^3$ | $353 \pm 177$ |
| e) | $1.62 \pm 0.09 \times 10^9$ | — | — | — | — | $83 \pm 58$ |
| TTMAB | | | | | | |
| a) | $1.38 \pm 0.04 \times 10^9$ | $1.33 \pm 0.09 \times 10^9$ | — | — | — | — |
| b) | $1.37 \pm 0.11 \times 10^9$ | — | — | — | — | $2.03 \pm 1.24 \times 10^3$ |
| c) | $1.3 \pm 0.05 \times 10^9$ | — | $1.06 \pm 0.08 \times 10^9$ | — | $6.06 \pm 9.13 \times 10^7$ | — |
| | 0 | 10 | 100 | 200 | 250 | 300 |
| DTMAB | | | | | | |
| a) | $1.59 \pm 0.18 \times 10^9$ | $1.44 \pm 0.07 \times 10^9$ | $1.3 \pm 0.03 \times 10^9$ | — | — | — |
| b) | $1.05 \pm 0.08 \times 10^9$ | — | — | — | — | — |
| c) | $1.25 \pm 0.08 \times 10^9$ | — | — | $8.75 \pm 1.28 \times 10^8$ | — | — |
| d) | $1.01 \pm 0.05 \times 10^9$ | — | — | — | $2.75 \pm 0.17 \times 10^8$ | $3.47 \pm 1.6 \times 10^5$ |
| DPC | | | | | | |
| a) | $1.59 \pm 0.27 \times 10^9$ | $1.39 \pm 0.34 \times 10^9$ | $9.8 \pm 2.17 \times 10^8$ | — | — | — |
| b) | $1.2 \pm 0.08 \times 10^9$ | — | $8.85 \pm 0.3 \times 10^8$ | $<10^5$ | — | — |
| | 0 | 20 | 22.5 | 25 | 27.5 | 30 |
| CPC | $1.69 \pm 0.23 \times 10^9$ | $1.84 \pm 0.087 \times 10^8$ | $9.07 \pm 2.16 \times 10^7$ | $5.15 \pm 1.18 \times 10^6$ | $1.98 \pm 0.36 \times 10^6$ | $8.93 \pm 0.99 \times 10^5$ |

| Compound | Concentration (ug/ml) | | |
|---|---|---|---|
| | 60 | 80 | 100 |
| HTMAB | | | |
| a) | — | — | $4.3 \pm 5.3 \times 10^4$ |
| b) | — | $1.39 \pm 2.08 \times 10^4$ | $9.52 \pm 16.4 \times 10^3$ |
| c) | $2 \pm 3$ | 0 | — |
| d) | — | — | — |
| e) | $30 \pm 40$ | 0 | — |
| TTMAB | | | |
| a) | — | — | 0 |
| b) | — | — | 0 |
| c) | $1.52 \pm 2.07 \times 10^3$ | $100 \pm 173$ | — |
| | 350 | 400 | 1000 |
| DTMAB | | | |
| a) | — | — | $100 \pm 100$ |
| b) | — | 0 | — |
| c) | — | 0 | — |
| d) | $800 \pm 1300$ | $117 \pm 161$ | — |
| DPC | | | |
| a) | — | — | 0 |
| b) | — | 0 | — |

TABLE D-2

Effect On Viability of Salmonella In Suspension

| Compound | $EC_{50}$ (±SD) $\underline{M} \times 10^{-5}$ | S (±SD) | # pts | r |
|---|---|---|---|---|
| CPC | $4.27 \pm 0.03$ | $6.55 \pm 0.15$ | 5 | .970 |
| HTMAB | $4.80 \pm 0.003$ | $7.0 \pm 0.03$ | 4 | 1.00 |
| TTMAB | $10.5 \pm 0.08$ | $2.6 \pm 0.03$ | 4 | .949 |
| DTMAB | $73 \pm 6.4$ | $9.1 \pm 7.2$ | 5 | .972 |

Based on the results in Table D-2, the quaternary ammonium compounds have the following order of potency in decreasing order: CPC>HTMAB>TTMAB>DTMAB. T tests showed these differences to be highly statistically significant (P≦0.001).

Figure 4:
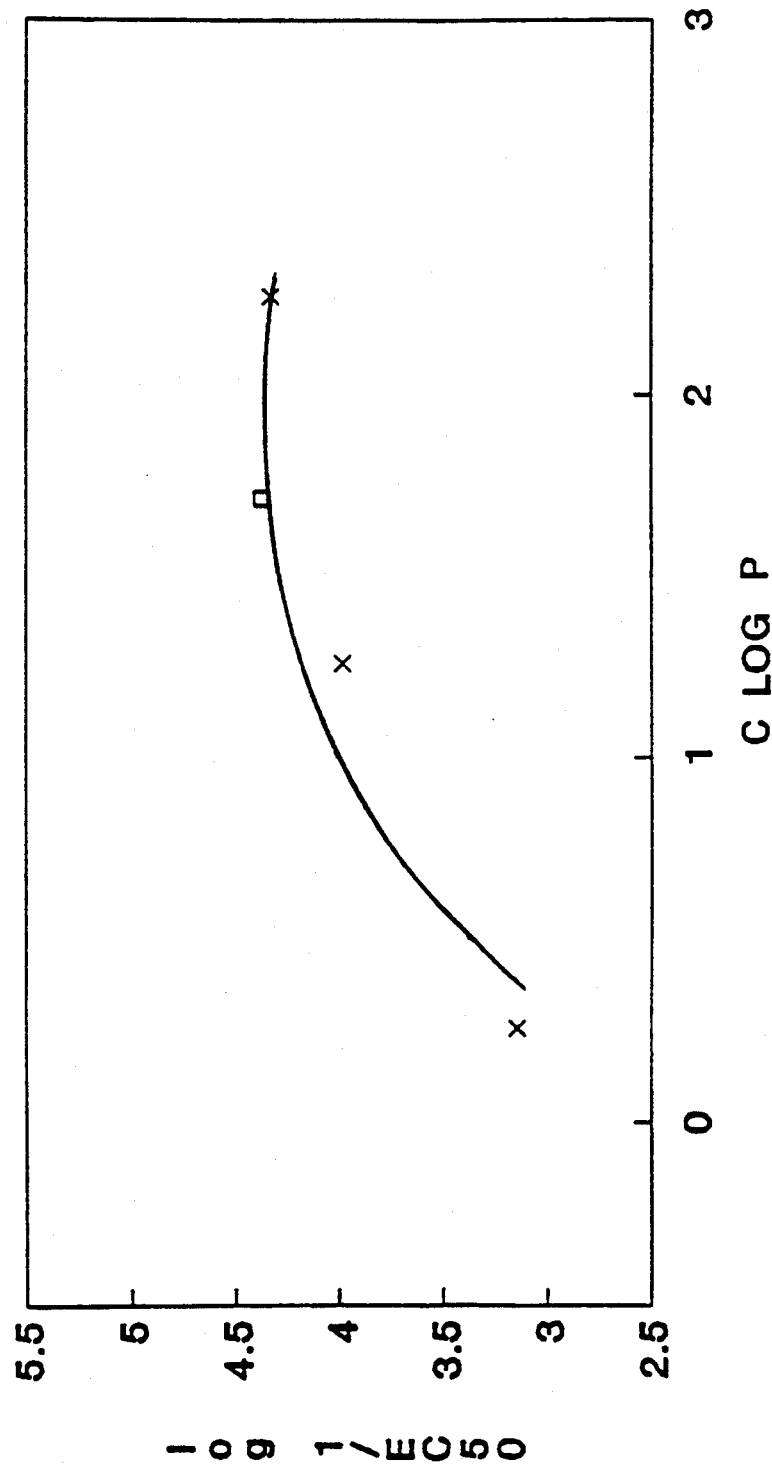
FIG. 4 is a graph illustrating the effect of hydrophobicity on the viability of *S. typhimurium*. The square symbol represents a pyridinium quaternary ammonium compound (CPC). The x symbol represents trimethyl quaternary ammonium compounds (DTMAB, TTMAB, and HTMAB).

Unlike the graph relating to detachment in FIG. 2, the trimethyl quaternary ammonium compounds (DTMAB, TTMAB, and HTMAB) and the pyridinium quaternary ammonium compounds for which $EC_{10}$ data were calculated, fall on the same parabolic curve with probable maximal activity of C log P around 2. This is illustrated in FIG. 4. These results suggests a difference in the mechanism of detachment and antibacterial effect for the quaternary ammonium compounds.

In addition to the quaternary ammonium compounds, the antimicrobial activities of chelating agents $Na_2$-EDTA and EGTA were investigated. $Na_2$-EDTA was purchased from the Sigma Chemical Company (St. Louis, Mo.). $Na_2$-EDTA was dissolved in 0.04 M PPB prior to the assay and further dilutions were made in the same buffer. As a chelating agent, EDTA is not considered to be bactericidal. By chelating trace metals that are necessary to microorganisms, however, EDTA may produce some ant±microbial activity.

EGTA was purchased from the Aldrich Chemical Company (Milwaukee, Wis.). EGTA was dissolved in 0.04 M PPB according to the procedure described by Harafuji and Ogawa (J. Biochem. 87:1305–1312 (1980)). After heating EGTA for 15 minutes at 80° C., the pH was adjusted to 7.0 by addition of NaOH. EGTA was filter-sterilized using a 0.2 μm Acro disc filter (Gelman Sciences; Ann Arbor, Mich.) prior to the assay. Further dilutions were made in sterile PPB. The results of these studies, in Table D-3, show that $Na_2$-EDTA and EGTA were ineffective against *S. typhimurium* in our model on viability testing.

TABLE D-3

Effect of Na$_2$-EDTA, and EGTA on viability of *Salmonella typhimurium* ATCC 14028. The bacterial viability is expressed as colony forming units per milliliter (CFU/ml). Values are the mean of three determinations (Mean ± SD).

| Compound | Concentration (μg/ml) | | | | |
|---|---|---|---|---|---|
| | 0 | 1,250 | 2,500 | 5,000 | 10,000 |
| Na$_2$-EDTA | 1.01 ± 0.03 × 10$^9$ | 9.48 ± 0.63 × 10$^8$ | 9.68 ± 0.16 × 10$^8$ | 9.89 ± 0.37 × 10$^8$ | 1.02 ± 0.04 × 10$^9$ |
| EGTA | 1.5 ± 0.05 × 10$^9$ | 1.55 ± 0.09 × 10$^9$ | 1.45 ± 0.03 × 10$^9$ | 1.51 ± 0.18 × 10$^8$ | 1.44 ± 0.15 × 10$^9$ |

Additional studies were conducted to evaluate the effect of chelating agents on the bactericidal activity of the quaternary ammonium cationic surfactants toward *S. typhimurium*. The chelating agents were combined with CPC before they were mixed with the cells in the treatment vial. As shown in Table D-3, the controls in which Na$_2$-EDTA and EGTA were tested alone showed no bactericidal effect. The effect of Na$_2$-EDTA or EGTA on the bactericidal activity of CPC toward *S. typhimurium* is shown in Table D-4. The activity of 20 μg/ml CPC with the organisms showed a 1.5-log decrease in CFU/ml. However, when CPC and Na$_2$-EDTA were used together, the cell viability decreased 2.5-fold. The combination of EGTA and CPC against *S. typhimurium* showed a less synergistic effect as compared to Na$_2$-EDTA and CPC. In view of the possible effect of Na$_2$-EDTA upon the cell wall of *S. typhimurium*, the results suggest that Na$_2$-EDTA may accelerate CPC action by increasing the permeability of the cell wall to CPC.

Protection 53(7):550–554 (1990)). Slides containing adherent cells were rinsed with 0.008 M PBS, at pH 7.2 to remove the unattached cells. The slides were then submerged in 200 ml of CPC at the appropriate dilution (50 to 1000 μg/ml) for 10 minutes. The solution was continuously stirred throughout the experiment. At the end of the reaction time, the slides were rinsed with PBS. Attached cells were removed by swabbing with a calcium alginate swab, followed by rinsing with PBS. The swab was partially dissolved by adding 0.5 ml of 10% sodium hexametaphosphate and vortexing for 1 minute. Cells were counted on tryptocase soy agar pour plates, which were incubated at 37° C. for 24 hours. Results are shown in Table E-1.

TABLE E-1

| Conc. CPC (μg/ml) | Colony Count (±SD) | P value |
|---|---|---|
| 0 (control) | 9.80 ± 2.95 × 10$^3$ | — |
| 5 | 2.52 ± 2.69 × 10$^3$ | 0.002 |
| 10 | 4.40 ± 5.68 × 10$^2$ | 0.002 |
| 50 | 2.0 ± 4.5 × 10$^1$ | 0.002 |

TABLE D-4

Effect of chelating agents on the bactericidal activity of cetylpyridinium chloride (CPC) toward *Salmonella typhimurium* ATC 14028. The bacterial viability is expressed as colony forming units per millimeter (CFU/ml). Values are the mean of three determinations (Mean ± SD)

| Chelating Agent | CPC Concentration (ug/ml) | | | | | |
|---|---|---|---|---|---|---|
| | 0 | 10 | 17 | 20 | 30 | 40 |
| 0 | | | | | | |
| a) | 9.68 ± 0.2 × 10$^8$ | — | — | 4.88 ± 2.23 × 10$^7$ | 117 ± 189 | — |
| b) | 6.64 ± 0.71 × 10$^8$ | 6.08 ± 0.6 × 10$^8$ | — | — | — | — |
| c) | 7.44 ± 0.35 × 10$^8$ | — | 7.25 ± 0.1 × 10$^7$ | — | — | — |
| 0.0625% Na$_2$-EDTA | | | | | | |
| a) | — | 6.21 ± 0.75 × 10$^8$ | — | — | — | — |
| b) | — | — | 3.24 ± 1.08 × 10$^7$ | — | — | — |
| 0.125% Na$_2$-EDTA | | | | | | |
| a) | — | 6.24 ± 0.79 × 10$^8$ | — | — | — | — |
| b) | — | — | 1.52 ± 0.42 × 10$^7$ | — | — | — |
| 0.25% Na$_2$-EDTA | | | | | | |
| a) | — | — | — | 4.13 ± 1.29 × 10$^6$ | 20 ± 13 | — |
| 0.5% Na$_2$-EDTA | | | | | | |
| a) | — | 5.79 ± 0.1 × 10$^8$ | — | — | — | — |
| b) | — | — | 4.8 ± 0.42 × 10$^6$ | — | — | — |
| 0 | | | | | | |
| a) | 1.27 ± 0.15 × 10$^9$ | — | — | 4.93 ± 0.12 × 10$^8$ | 82 ± 73 | — |
| b) | 1.47 ± 0.05 × 10$^9$ | — | — | 1.26 ± 0.25 × 10$^8$ | — | 8 ± 14 |
| 0.25% EGTA | | | | | | |
| a) | — | — | — | 3.01 ± 0.44 × 10$^8$ | 85 ± 65 | — |
| 1% EGTA | | | | | | |
| b) | — | — | — | 2.64 ± 0.32 × 10$^7$ | — | 0 |

EXAMPLE 5

The Effect of Viability of Salmonella In Surface-Adherent Microcolonies

Detachment of adherent *S. typhimurium* from microscope slides by CPC was studied using modifications to the method of Frank et al. ("Surface-Adherent Growth of *Listeria monocytogenes* is Associated With Increased Resistance to Surfactant Sanitizers and Heat", J. Food As shown in Table E-1, CPC exhibited a substantial effect against surface adherent microcolonies of Salmonella. These microcolonies usually form an impenetrable wall around themselves, thus making them quite resistant to killing under usual circumstances.

Adherent cells were completely inactivated (99.8%) by the 10 minute exposure to 50 μg/ml CPC concentrations. At the 50 μg/ml level CPC showed a 3½ log decrease in the number of Salmonella microcolonies.

This effect is quite important in dealing with Salmonella contamination that has occurred over a long period of time and prior to the animal (meat source) reaching the food processing plant. In these experiments, microcolony populations per slide were tenfold lower as compared to results reported in the literature. (See Frank et al.).

EXAMPLE 6

A. Effect of Surfactants on the Attachment of Salmonella typhimurium to Chicken Skin The following experiments utilizing chicken legs were conducted to determine the killing potential of a variety of surfactants against Salmonella on the skin and free in solutions. To this end, chicken legs obtained from the Department of Agriculture at the University of Arkansas, Fayetteville, were incubated for thirty minutes at room temperature with a 1:5000 dilution of *Salmonella typhimurium*. The chicken legs were removed five at a time and then rinsed twice in tap water to remove the unattached and excess Salmonella. The rinse water was sampled, diluted, and then plated onto XLD pour plates. Chicken legs were further incubated for 60 minutes at 4° C. in a chemical surfactant at a dilution of 0.1%, 0.5%, and 1.0%. The chicken legs were then removed and rinsed twice in tap water to remove the released Salmonella and excess chemicals. Rinses were then sampled, diluted, and then plated onto XLD pour plates.

The chicken legs were then individually washed with 100 ml sterile double distilled water, and then shaken fifty times. Samples of the wash H₂O were diluted and plated onto XLD pour plates. The chicken legs were further swabbed after the washing step above. The swabs were then plated onto the XLD plates. A set of wash samples were enriched with TT Broth Base Hajna and then plated onto XLD plates.

All of the samples were plated in 1 ml aliquots onto XLD pour plates. A positive control sample incubated in sterile double distilled water at 4° C. was run for each of the aforementioned conditions. The results are shown in Tables F-1 through F-4. Treatments occurred at both 4° C. and 25° C. The data is reported as the mean number of CFU/ml. The ratio in the table represents the number of chicken legs out of a sample of ten chicken legs producing the notated number of colonies, as indicated by the +, ++, +++, or ++++.

As shown in Tables F-1 and F-4, results demonstrate that the cationic surfactants killed Salmonella both free in solution and those attached to the chicken skin. On the other hand, nonionic and anionic surfactants did not kill the Salmonella either on the chicken skin or free in solution. In interpreting the above results, particular attention should be given to the values in the columns labeled "SWABS" Swabbing of the chicken skin is the test of contamination not removed by treatment with a surfactant followed by washing and rinsing. It is the microbial contamination that remains on the tissue after treatment and is the source of possible illness in people who consume a meat product. Cationic surfactants, particularly CPC, were found to be superior at both temperatures tested for reversing Salmonella contamination of chicken skin.

TABLE F1

| | CATIONIC SURFACTANTS UTILIZING DRUMSTICKS 4° C. | | | | |
|---|---|---|---|---|---|
| | Surfactant Solution | Rinse H₂O | Wash H₂O | Swabs | Enrichment |
| Benzalkonium Chloride | | | | | |
| 0.1% | 0 | + | +4/10 | +6/10 | 1/10 |
| 0.5% | 0 | 0 | 0 | +1/10 | 1/10 |
| 1.0% | 0 | 0 | 0 | ++1/10 | 0/10 |
| Positive Control | ++ | + | ++10/10 | +++10/10 | 7/10 |
| Benzethenium Chloride | | | | | |
| 0.1% | 0 | + | +1/10 | ++9/10 | 2/10 |
| 0.5% | 0 | + | 0/10 | ++8/10 | 0/10 |
| 1.0% | 0 | + | 0/10 | ++5/10 | 0/10 |
| Positive Control | ++ | + | +++10/10 | +++10/10 | 10/10 |
| Cetylpyridinium Chloride | | | | | |
| 0.1% | 0 | 0 | +8/10 | +8/10 | 8/10 |
| 0.5% | 0 | 0 | +7/10 | +9/10 | 9/10 |
| 1.0% | 0 | 0 | +9/10 | +5/10 | 5/10 |
| Positive Control | ++ | + | ++10/10 | +++10/10 | 10/10 |

+(1-10); ++(11-100); +++(101-300); ++++(TNTC)

TABLE F2

| | ANIONIC SURFACTANTS UTILIZING DRUMSTICKS 4° C. | | | | |
|---|---|---|---|---|---|
| | Surfactant Solution | Rinse H₂O | Wash H₂O | Swabs | Enrichment |
| Sodium Dodecylsulfate | | | | | |
| 0.1% | ++ | ++ | ++10/10 | ++10/10 | 10/10 |
| 0.5% | ++ | + | ++10/10 | ++10/10 | 10/10 |
| 1.0% | + | + | ++10/10 | ++10/10 | 10/10 |
| Positive Control | ++ | + | ++10/10 | ++10/10 | 10/10 |
| Tergitol 4 | | | | | |
| 0.1% | ++ | ++ | ++10/10 | ++10/10 | 10/10 |
| 0.5% | ++ | + | ++10/10 | ++10/10 | 10/10 |

TABLE F2-continued

ANIONIC SURFACTANTS UTILIZING DRUMSTICKS
4° C.

|  | Surfactant Solution | Rinse H₂O | Wash H₂O | Swabs | Enrichment |
|---|---|---|---|---|---|
| 1.0% | ++ | ++ | ++10/10 | ++10/10 | 10/10 |
| Positive Control | ++ | + | ++10/10 | ++10/10 | 10/10 |
| Deoxycholic Acid | | | | | |
| 0.1% | ++ | + | ++10/10 | ++10/10 | 10/10 |
| 0.5% | + | + | ++10/10 | +10/10 | 10/10 |
| 1.0% | ++ | + | ++10/10 | ++9/10 | 10/10 |
| Positive Control | ++ | + | +++10/10 | ++9/10 | 10/10 |

+(1-10); ++(11-100); +++(101-300); ++++(TNTC)

TABLE F3

NONIONIC SURFACTANTS UTILIZING DRUMSTICKS
4° C.

|  | Surfactant Solution | Rinse H₂O | Wash H₂O | Swabs | Enrichment |
|---|---|---|---|---|---|
| Tergitol NP40 | | | | | |
| 0.1% | ++ | + | ++10/10 | ++10/10 | 10/10 |
| 0.5% | ++ | + | ++9/10 | ++10/10 | 10/10 |
| 1.0% | ++ | + | ++10/10 | +++10/10 | 10/10 |
| Positive Control | ++ | + | ++10/10 | ++10/10 | 10/10 |
| Tween 20 | | | | | |
| 0.1% | +++ | + | ++7/10 | ++10/10 | 10/10 |
| 0.5% | +++ | + | ++10/10 | ++10/10 | 10/10 |
| 1.0% | +++ | + | ++6/10 | ++10/10 | 10/10 |
| Positive Control | ++ | + | ++10/10 | ++10/10 | 10/10 |
| Tergitol NP7 | | | | | |
| 0.1% | ++ | + | ++10/10 | ++10/10 | 10/10 |
| 0.5% | ++ | + | ++9/10 | ++10/10 | 10/10 |
| 1.0% | ++ | + | ++9/10 | ++9/10 | 10/10 |
| Positive Control | +++ | 0 | +++10/10 | ++9/10 | 10/10 |

+(1-10); ++(11-100); +++(101-300); ++++(TNTC)

TABLE F4

CATIONIC SURFACTANTS UTILIZING DRUMSTICKS
25° C.

|  | Surfactant Solution | Rinse H₂O | Wash H₂O | Swabs | Enrichment |
|---|---|---|---|---|---|
| Dodecylpyridinium Chloride | | | | | |
| .01% | 0 | + | ++10/10 | +6/10 | 10/10 |
| 0.1% | 0 | 0 | ++7/10 | 0/10 | 8/10 |
| 1.0% | 0 | 0 | 0 | 0/10 | 0/10 |
| Positive Control | ++ | + | ++10/10 | ++10/10 | 10/10 |
| Dodecyltrimethyl Ammonium Bromide | | | | | |
| .01% | + | + | ++10/10 | +10/10 | 10/10 |
| 0.1% | 0 | + | ++10/10 | +6/10 | 8/10 |
| 1.0% | 0 | 0 | 0 | 0/10 | 0/10 |
| Positive Control | ++ | + | ++10/10 | ++10/10 | 10/10 |
| Tetradecyltrimethyl Ammonium Bromide | | | | | |
| .01% | 0 | + | ++10/10 | +10/10 | 8/10 |
| 0.1% | 0 | ++ | 0 | +5/10 | 0/10 |
| 1.0% | 0 | 0 | 0 | 0/10 | 0/10 |
| Positive Control | ++ | + | ++10/10 | ++10/10 | 10/10 |
| Hexadecyltrimethyl Ammonium Bromide | | | | | |
| .01% | 0 | + | ++10/10 | +9/10 | 5/10 |
| 0.1% | 0 | + | 0 | +6/10 | 5/10 |
| 1.0% | 0 | 0 | 0 | +3/10 | 0/10 |
| Positive Control | ++ | + | ++10/10 | ++10/10 | 10/10 |
| Cetylpyridinium Chloride | | | | | |
| .01% | 0 | + | +++10/10 | ++9/10 | 10/10 |
| .05% | 0 | 0 | ++10/10 | +9/10 | 7/10 |
| 0.1% | 0 | 0 | ++8/10 | +7/10 | 0/10 |
| Positive Control | +++ | ++ | +++10/10 | +++10/10 | 10/10 |

+(1-10); ++(11-100); +++(101-300); ++++(TNTC)

B. Detachment and Attachment Prevention Studies of *Salmonella typhimurium* Utilizing Skin Excised from Drum Sticks To determine the ability of surfactants to inhibit attachment or produce detachment of Salmonella, the following experiment was conducted. A hole was bored into the bottom of a 150 ml specimen cup. Chicken skin was excised from a drum stick and then placed over the cap of the specimen cup, and then the cap was screwed on. *S. typhimurium* was diluted 1:5000 with PBS or a surfactant. The surfactants were diluted appropriately. The skin was then inoculated with the solution containing the *S. typhimurium* and the surfactant for 30 minutes at room temperature.

Following incubation, the skin was washed. The rinse water was diluted appropriately in PBS and then plated onto XLD pour plates. The *S. typhimurium* was counted and reported as CFU/ml. The skin was swabbed so as to remove any remaining *S. typhimurium* using a nitrocellulose lift and the CFU's/ml on the lift were also counted. The results are shown in Table F-5 below.

As shown, prevention of the attachment of *S. typhimurium* on chicken skin occurred only with the cationic surfactants. Two quaternary ammonium cationic surfactants, CPC and benzelthonium chloride were found to be the most effective in preventing Salmonella contamination of chicken skin. The nonionic and anionic surfactants that were tested showed no effect on preventing attachment.

Toxicology, Inc. (Anapolis, Md.). Dimethylsulfoxide (DMSO) solutions of CPC were prepared at concentrations ranging from 1 to 50 µg/ml.

Bacterial broth cultures were grown overnight at 37° with shaking in Oxoid Broth #2. For assays in the absence of S9, a 0.5 ml aliquot of 100 mM Sodium Phosphate Buffer, pH 7.4, was added to sterile 13×100 mm capped culture tubes. For assays in the presence of S9, a 0.5 ml aliquot of 10% S9 mix was added. The S9 mix consisted of 8 mM magnesium chloride, 33 mM potassium chloride, 5 mM glucose-6-phosphate, 4 mM NADP, 100 mM sodium phosphate, pH 7.4 and S9 in a concentration of approximately 1.46 mg protein/ml.

The culture tubes were placed in an ice bath and 0.1 ml of the bacterial suspension and 0.1 ml of a DMSO solution of the test compound were added. The mixture was vortexed gently and incubated at 37° for 20 minutes with shaking in a water bath. Molten top agar (2.0 ml) containing 0.5 mM histidine HCl and 0.5 mM biotin were added, and the mixture was vortexed gently and poured onto a minimal glucose plate. After allowing the agar to solidify, the plates were inverted and placed in a 37° incubator in the dark for 48 hours. The revertant (mutant) colonies were counted and the background lawn was examined on all plates. All assays were performed in triplicate and the results are shown in Table G1 as mean±s.d. A response that was two times that of the DMSO solvent control was considered a positive response.

TABLE F5
EFFECT OF VARIOUS SURFACTANTS ON PREVENTING ATTACHMENT OF *SALMONELLA TYPHIMURIUM* ON CHICKEN SKIN

| | Anionic Surfactants | | | | | |
|---|---|---|---|---|---|---|
| | Tergitol 4 | Control | Deoxycholic Acid | Control | Sodium Dodecyl Sulfate (SDS) | Control |
| CFU/ml on XLD agar | 4/$10^2$ | 1 × $10^2$ | 90 | 40 | 4 × $10^2$ | OG(2) |
| Nitrocellulose lift (# of colonies) | TNTC[a] | TNTC | OG[b] | TNTC | TNTC | TNTC |

| | Cationic Surfactants | | | | | |
|---|---|---|---|---|---|---|
| | Cetylpyridinium Chloride | Control | Benzethonium Chloride | Control | Benzalkonium Chloride | Control |
| CFU/ml on XLD agar | 20 | 2.9 × $10^2$ | 10 | 4.9 × $10^2$ | 0 | 40 |
| Nitrocellulose lift (# of colonies) | 4 | TNTC | 250 | TNTC | OG(R)[c] | TNTC |

| | Nonionic Surfactants | | | | | |
|---|---|---|---|---|---|---|
| | Tergitol NP7 | Control | Tergitol NP40 | Control | Tween 20 | Control |
| CFU/ml on XLD agar | 3 | R+ | 0 | 9 | 2 × $10^2$ | 6 × $10^1$ |
| Nitrocellulose lift (# of colonies) | TNTC | TNTC | TNTC | TNTC | TNTC | TNTC |

[a]TNTC: Too numerous to count.
[b]Areas of overgrowth as seen by H.S production were also on these plates. The colonies within these areas were uncountable, gridded areas covered were counted.
[c]R-Rim growth - uncountable.

EXAMPLE 7

Salmonella Reversion Assay of Cetylpyridinium Chloride

The mutagenicity of cetylpyridinium chloride (CPC) was evaluated in Salmonella typhimurium by the preincubation method as described by Maron and Ames ("Revised Methods for the Salmonella Mutagenicity Tests," Mutation Research, 113:173-215 (1983)). Test strains TA98 and TA100 were obtained from Bruce N. Ames (University of California, Berkley, Calif.). Mutagenicities were determined both in the absence of and in the presence of a mammalian liver S9 activating system. S9 is the 9000×g supernatant prepared from liver homogenates from Aroclor 1254 stimulated male Sprague Dawley rats. The S9 was purchased from Molecular Mutagenicity Evaluation of Cetylpyridinium Chloride in the Salmonella Reversion Assay

| Cetylpyridinium Chloride | Revertants/plate | | | |
|---|---|---|---|---|
| | TA98[a] | | TA100[b] | |
| µg/plate | −S9 | +S9 | −S9 | +S9 |
| 1 | 24 ± 3 | 25 ± 2 | 98 ± 5 | — |
| 5 | 18 ± 4 | 28 ± 1 | 133 ± 5 | 129 ± 14 |
| 10 | — | 25 ± 3 | 130 ± 9 | 136 ± 11 |
| 20 | B[c] | 28 ± 2 | B[c] | 126 ± 14 |
| 40 | — | 30 ± 1 | B[c] | 125 ± 5 |

TABLE G1-continued

Mutagenicity Evaluation of Cetylpyridinium Chloride
in the Salmonella Reversion Assay

| Cetylpyridinium Chloride µg/plate | Revertants/plate | | | |
|---|---|---|---|---|
| | TA98[a] | | TA100[b] | |
| | −S9 | +S9 | −S9 | +S9 |
| 50 | B[c] | 35 ± 6 | B[c] | 126 ± 10 |

[a]TA98 control reversion frequencies: DMSO were 18 ± 1 (−S9) and 26 ± 3 (+S9); Niridazole (0.2 µg/plate) 358 ± 19 (−S9); and 2-aminoanthracene (2.5 µg/plate) 901 ± 90 (+S9).
[b]TA100 control reversion frequencies: DMSO 111 ± 20 (−S9) and 125 ± 5 (+S9); Niridazole (0.2 µg/plate) 637 ± 57 (−S9); and 2-aminoanthracene (2.5 µg/plate) 1497 ± 68 (+S9).
[c]Bactericidal response The data in Table G1 show that at low concentrations, CPC is nonmutagenic in either TA98 or TA100 in the absence of the S9 mammalian activating system. However as the concentration increases above 10 µg/plate, a bactericidal response is produced. In the presence of the S9 homoginate, CPC was neither mutagenic nor cytotoxic, suggesting that mammalian metabolism of the CPC results in detoxification.

EXAMPLE 8

Salmonella Reversion Assay of Cetylpyridinium Chloride After Heating at 205° C.

The mutagenicity of cetylpyridinium chloride (CPC) heated at 205° C. for 30 minutes in vegetable oil was evaluated in *Salmonella typhimurium*. Test strains TA98 and TA100 were used. Again, mutagenicities were determined both in the absence and in the presence of the mammalian liver S9 activating system.

Solutions of CPC (0.001% to 0.1%) were prepared in vegetable oil (Chef-Way ®, Riceland Foods, Inc., Stuttgart, Ariz.). These solutions were heated at 205° C. for 30 minutes to simulate conditions that would occur during the frying of a meat in which CPC had not been completely removed. The vegetable oil/CPC solutions were diluted 1:10 with dimethylsulfoxide (DMSO) to mixtures containing 0.0001 to 0.01% CPC.

The assays were performed according to the method described in Example 7. All assays were performed in triplicate and the results are shown as mean±s.d. as shown in Table H1. A response that was two times that of the solvent control was considered a positive response.

TABLE H1

Mutagenicity In Salmonella of Cetylpyridinium Chloride Previously Heated at 205° C.

| Cetylpyridinium Chloride µg/plate | Revertants/plate | | | |
|---|---|---|---|---|
| | TA98[a] | | TA100[b] | |
| | −S9 | +S9 | −S9 | +S9 |
| 0.1 | 16 ± 3 | 26 ± 4 | 117 ± 6 | 122 ± 3 |
| 1.0 | 20 ± 5 | 20 ± 1 | 113 ± 8 | 126 ± 14 |
| 5.0 | 22 ± 3 | 25 ± 4 | 123 ± 4 | 118 ± 10 |
| 10.0 | 25 ± 3 | 22 ± 3 | 126 ± 4 | 123 ± 8 |

[a]TA98 control reversion frequencies: DMSO were 25 ± 2 (−S9) and 23 ± 4 (+S9); Niridazole (0.2 µg/plate) 126 ± 7 (−S9); and 2-aminoanthracene (2.5 µg/plate) 909 ± 85 (+S9).
[b]TA100 control reversion frequencies: DMSO 108 ± 7 (−S9) and 122 ± 16 (+S9); Niridazole (0.2 µg/plate) 729 ± 30 (−S9); and 2-aminoanthracene (2.5 µg/plate) 1103 ± 84 (+S9).

During the process of heating CPC in vegetable oil, the oil darkened. This effect appeared to be a function of the concentration of CPC in the oil. However, the mutagenicity data as shown in Table H1 for all concentrations tested demonstrates t-hat heating CPC in vegetable oil did not produce substances which are mutagenic in either TA98 or TA100 either in the absence or presence of the S9 mammalian activating system.

EXAMPLE 9

Observational Data

No deleterious effects were observed from exposure of chicken skin to the quaternary ammonium cationic surfactants. No changes in odor, color, texture, or appearance were visible or detected throughout the experiments discussed hereinabove.

It should be understood that various changes and modifications to the presently preferred embodiments described herein will be apparent to those skilled in the art. Such changes and modifications can be made without departing from the spirit and scope of the present invention, and without diminishing its attendant advantages. It is therefore intended that such changes and modifications be covered by the appended claims.

We claim:

1. A method for removing Salmonella contamination from meat products during processing, comprising the step of:
    treating a meat product with an effective amount of a quaternary ammonium compound in an aqueous solution to remove Salmonella contamination.

2. The method of claim 1, wherein the meat product is poultry.

3. The method of claim 1, wherein the alkylpyridinium is selected from the group consisting of cetylpyridinium chloride, cetylpyridinium bromide, and dodecylpyridinium chloride.

4. The method of claim 1, wherein the preferred quaternary ammonium compound is cetylpyridinium chloride.

5. The method of claim 1, wherein the preferred quaternary ammonium compound is cetylpyridinium bromide.

6. The method of claim 1, wherein the quaternary ammonium compound is a cationic surfactant.

7. The method of claim 1, wherein the effective amount of the quaternary ammonium compound ranges from approximately $1 \times 10^{-6}$ M to $4 \times 10^{-4}$ M.

8. The method of claim 1, wherein the treating step is performed at a temperature ranging from approximately 4° C. to about 100° C.

9. The method of claim 1, wherein the treating step is performed for approximately 10 minutes to about 60 minutes.

10. A method for preventing Salmonella contamination of meat products during processing, comprising the step of:
    treating a meat product with an effective amount of a composition consisting essentially of an alkylpyridinium quaternary ammonium compound in an aqueous solution to prevent Salmonella contamination.

11. The method of claim 1, wherein the meat product is poultry.

12. The method of claim 10, wherein the alkylpyridinium is selected from the group consisting of cetylpyridinium chloride, cetylpyridinium bromide, and dodecylpyridinium chloride.

13. The method of claim 10, wherein the preferred quaternary ammonium compound is cetylpyridinium chloride.

14. The method of claim 10, wherein the preferred quaternary ammonium compound is cetylpyridinium bromide.

15. The method of claim 10, wherein the quaternary ammonium compound is a cationic surfactant.

16. The method of claim 10, wherein the effective amount of the quaternary ammonium compound ranges from approximately $1 \times 10^{-6}$ M to $4 \times 10^{-4}$ M.

17. The method of claim 10, wherein the treating step is performed at a temperature ranging from approximately 4° C. to about 100° C.

18. The method of claim 10, wherein the treating step is performed for approximately 10 minutes to about 60 minutes.

* * * * *